United States Patent [19]

Matsuki et al.

[11] Patent Number: 4,607,790
[45] Date of Patent: Aug. 26, 1986

[54] CYCLE SEQUENCE TIME/TEMPERATURE CONTROLLER

[75] Inventors: Hiroshi Matsuki; Takao Sumiyoshi, both of Tokyo, Japan

[73] Assignee: Suga Test Instruments Co., Ltd., Tokyo, Japan

[21] Appl. No.: 706,299

[22] Filed: Feb. 27, 1985

[30] Foreign Application Priority Data

Jul. 20, 1984 [JP] Japan ................................ 59-149705

[51] Int. Cl.⁴ ............................................. G05D 23/00
[52] U.S. Cl. ..................................... 236/94; 73/336.5; 236/44 C; 364/506
[58] Field of Search ..................... 236/94, 44 C, 44 R; 165/11 R; 73/336.5, 338, 338.3; 364/557, 506

[56] References Cited

U.S. PATENT DOCUMENTS 3,599,862  8/1971  Hogan ................................. 73/336.5
3,825,723  7/1974  Roeser ............................... 236/44 C

*Primary Examiner*—William E. Wayner
*Attorney, Agent, or Firm*—Wenderoth, Lind & Ponack

[57] ABSTRACT

A cycle time/temperature controller for a combination corrosion tester includes a device for setting a loop number and a number of repetitions of that loop, a device for setting a sequence of test items within a loop including: a test temperature, a test humidity, and an operating time; the controller also includes a generator for generating an operative signal and a device for enabling the start of operation according to an external start signal and an output circuit for outputting a contact output corresponding to each test item for the set operating time; adjustment outputs for dry bulb and wet bulb temperatures are also provided, each output providing adjustments at the set test temperature and the set test humidity. The controller displays the current loop number and the number of repetitions and also displays: the test item number, the dry bulb temperature, the wet bulb temperature, the wet bulb temperature or humidity, and the time elapsed, during its operation.

1 Claim, 6 Drawing Figures

CYCLE SEQUENCE TIME/TEMPERATURE CONTROLLER

BACKGROUND OF THE INVENTION

1. Field of the Invention

This invention relates generally to the operational control of a combination corrosion tester for actively testing what level of durability industrial materials or products exhibit because of natural phenomena under various environmental conditions.

2. Description of the Prior Art

A combination corrosion tester establishes specific environmental conditions inside one or a plurality of testing tanks in accordance with stipulated test conditions of a brine spray test, a dry test, a wet test, a low-temperature test, a dew test, an immersion test, a photoradiation test, etc., by providing a variety of controls. These tests are performed in accordance with a designated sequence for designated periods of time, and the tests are repeated a designated number of times in order to examine the durability of each testpiece. Recently, single-cycle tests, in which the test items are put in sequence and repeated, have proved to be insufficient for obtaining results close to those of complicated natural phenomena, and hence combinations of complicated cycles are now required. The requirements are not limited to combinations of cycles alone, but also necessitate testing methods in which set conditions of temperature and humidity of the same test item are changed during a cycle, and in which temperature control is effected in such a fashion that the temperature is gradually raised or reduced to target values with the passage of time, in addition to tests under a predetermined constant temperature.

In order to satisfy these requirements by conventional methods, a number of timers and temperature controllers corresponding to the test items must be added to the controller, and to assemble loops of repeated cycles, a number of preset counters corresponding to the number of loops must also be added to the apparatus. Furthermore, if the several levels of temperature must be set, the same number of temperature controllers as stages is necessary. From the programming point of view, a program controller is also necessary if control must be made while determining the gradients of temperature rises and falls. In addition to the problem that an enormous number of components are necessary, this results in the critical problem that if the circuitry is designed with a loop configuration governing the components, the apparatus can set and change only the selection and sequence of test items, the test time, the testing temperature, and the number of loops. It is almost impossible, in accordance with conventional methods, to freely change the loop configuration, and in order to accomplish such an object, the circuit must be redesigned from scratch, with the consequent necessity of changing wiring or connections.

One of the methods of providing the temperature control described above is a so-called "program control" which is employed when it is desired to gradually change the tempeature with the passage of time, and which uses commercially-available cam controllers, gear controllers, photoelectric controllers or any of various other types of controllers. However, all of these are expensive, and can not be operated easily by just a key operation, although program changes are possible. Moreover, if a pattern which differs from one test item to another is required during a cycle, adjusters must be aligned for each pattern. In addition, the conventional system is not advantageous from the viewpoints of both space and cost.

SUMMARY OF THE INVENTION

In order to eliminate the problems described above, the inventor of the present invention previously filed an application (Japanese Patent Application No. 083402/1983) entitled "Cycle sequence time setter" which makes it possible to freely program the loop configuration, the test items, the test time, etc., and which can make the control method of a combination corrosion tester much more convenient.

The present invention adds the function of temperature and humidity control to the "Cycle sequence time setter" of the prior application. In other words, the dry bulb temperature, the humidity, and the test time can be set in accordance with a given test item. The usual method of setting humidity involves reading the wet bulb temperature corresponding to the desired humidity from a relative humidity table of dry bulb temperatures and corresponding wet bulb temperatures, and then seting that temperature in a temperature controller for the wet bulb thermometer. In the present invention, however, even when the relative humidity is set directly, the wet bulb temperature can be automatically calculated within the apparatus. It is, of course, possible to set the wet bulb temperature, and in such a case, the relative humidity can be directly read out during the operation in the same way.

In addition to a constant value control in which temperature is controlled to a constant set value, the present invention turns the temperature control system into a program control system in which a given temperature is changed from $C_1$ to another temperature $C_2$ during a period of time $t_1$. Therefore, the present invention provides a controller which can cope with any practical tests carried out by a combination corrosion tester, by preparing a simple program.

These and other objects and featurs of the present invention will become more apparent from the following description, taken in conjunction with the accompanying drawings.

DESCRIPTION OF THE PREFERRED EMBODIMENT

It is noted that a detailed description of the various individual elements comprising the preferred embodiment described below have been omitted for the sake of brevity. It is to be understood that all of such elements are commercially available items which could be easily selected and combined in accordance with the description below by one skilled in the art without undue experimentation.

Figure 3:
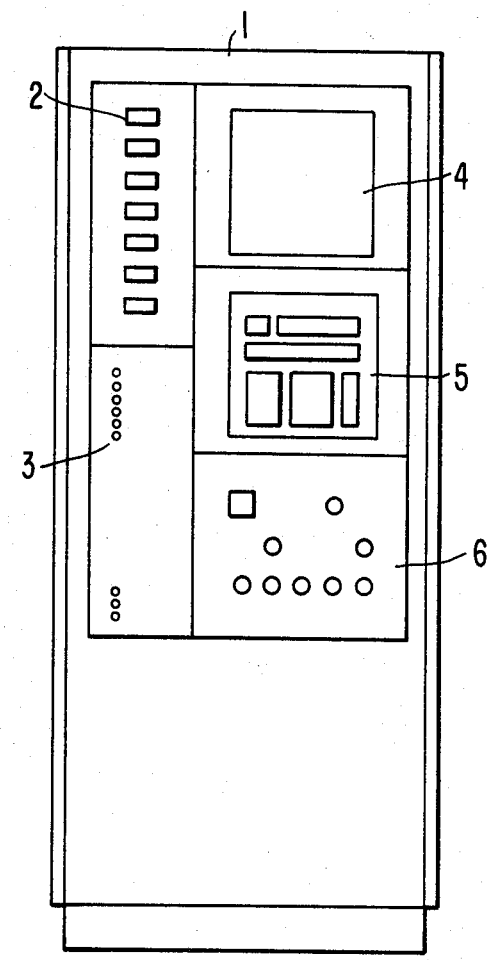
FIG. 3 shows a front view of the control panel of a combination corrosion tester using the cycle sequence time/temperature controller of the present invention.

One preferred embodiment of the invention will now be described in detail with reference to FIGS. 1 through 6. FIG. 3 shows an example of the control panel of a combination corrosion tester using the apparatus of the present invention. It consists of a casing 1, operation indicator lamps 2, a group of safety indicator lamps 3, a temperature recorder 4, a cycle sequence time/temperature controller 5 of the present invention, operating switches 6, etc. It can be understood that, in comparison with the control panel of the conventional system disclosed in a prior patent application (Japanese Patent Application No. 083402/1983), the construction is greatly simplified.

Figure 1:
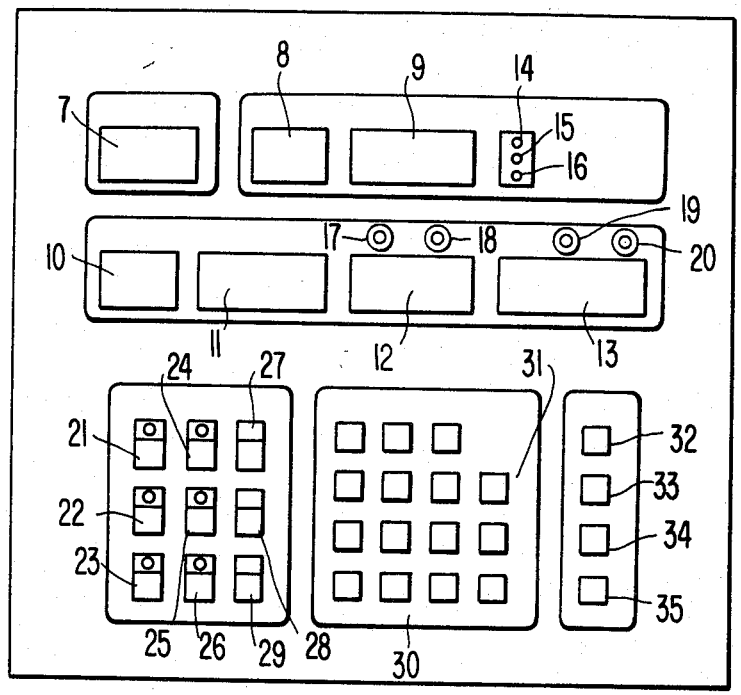
FIG. 1 shows a front panel of a cycle sequence time/temperature controller in accordance with the present invention.

FIG. 1 is a front patent view of the apparatus 5 of the present invention housed in its casing. In FIG. 1, a display window 7 shows the program sequence, and a display window 8 shows the loop number. A display window 9 shows the number of repeats of that loop, and a display window 10 shows the test item number. A display window 11 shows dry bulb temperature, and a display window 12 shows wet bulb temperature or relative humidity. A display window 13 shows the test time. Of these windows 7 through 13, the windows 9, 11, 12, and 13 show set values in a setting mode which will be described below, and current values during operation. When the current time is displayed, the display window 13 showing the test time displays the time in terms of the balance obtained by reducing the time elapsed from a set time, so that the time until the completion of the current test item can be conveniently comprehended at first glance.

An indicator lamp 14 indicates an "instantaneous operation" condition in which the measurement of the test time starts simultaneously with a change-over of test items. An indictor lamp 15 which indicates that a particular condition has been achieved indicates a condition achieved when the measurement of a test time starts from the point of time at which the temperature of a test item has reached a predetermined value, after a change-over of test items. An indicator lamp 16 which indicates program control indicates that a shift in the set value of the temperature is in an operating condition of program control which will be described below.

Of the indicator lamps 17 and 18, lamp 17 is turned on when the numeric value indicated in the display window 12 showing either wet bulb temperature or relative humidity is wet bulb temperature, and lamp 18 is turned on when the numeric value is relative humidity. A temperature/humidity selector switch 31 selects these indicator lamps. The indicator lamps 17 and 18 are alternately turned on whenever the switch 31 is operated, and the display of the display window 12 is changed between wet bulb temperature and relative humidity in response thereto. An indicator lamp 19 indicates that the time units are "hours", and an indicator lamp 20 indicates that the time units are "minutes". The "hours" and "minutes" units are alternately changed over whenever an hour/minute selector switch 32 is pressed. Within a series of programs, however, one of these units is used alone.

Switches provided with indicator lamps 21 through 26 are used to change over between operating modes. The switches include "display" 21 (which is set at the start of, and during, the operation), "set" 22 (a mode for setting a new program), "confirmation" 23, "change" 24, "insert" 25 and "delete" 26. A switch 27 is used to specify "loop start", a switch 28 "loop end", and a "test" switch 29 the test item number. Numeral switches "0" to "9", a decimal point switch, a "-" switch and a "correction" set switch are arranged in a group of numeric keys 30. Of these, the "correction" (set) switch differs from the "set" switch 22 of the operating mode, it is used to specify the end of a numeral when the numeric keys are present. Numerals which have already been input are processed as a series of numeric values only after this switch is pressed.

Condition-setting switches 33 through 35 correspond to indicator lamps 14 through 16, respectively. An "instantaneous operation" specification switch 33 corresponds to the "instantaneous operation" indicator lamp, an "after condition achieved" specification switch 34 corresponds to the indictaor lamp 15, and a "program control" specification switch 35 corresponds to the indicator lamp 16. They are used to specify those operations.

All the items necessary for various cycle operations can be set using these indicators and switches, and the apparatus of the present invention can easily be programmed to cope with any testing conditions, however complicated.

Figure 2:
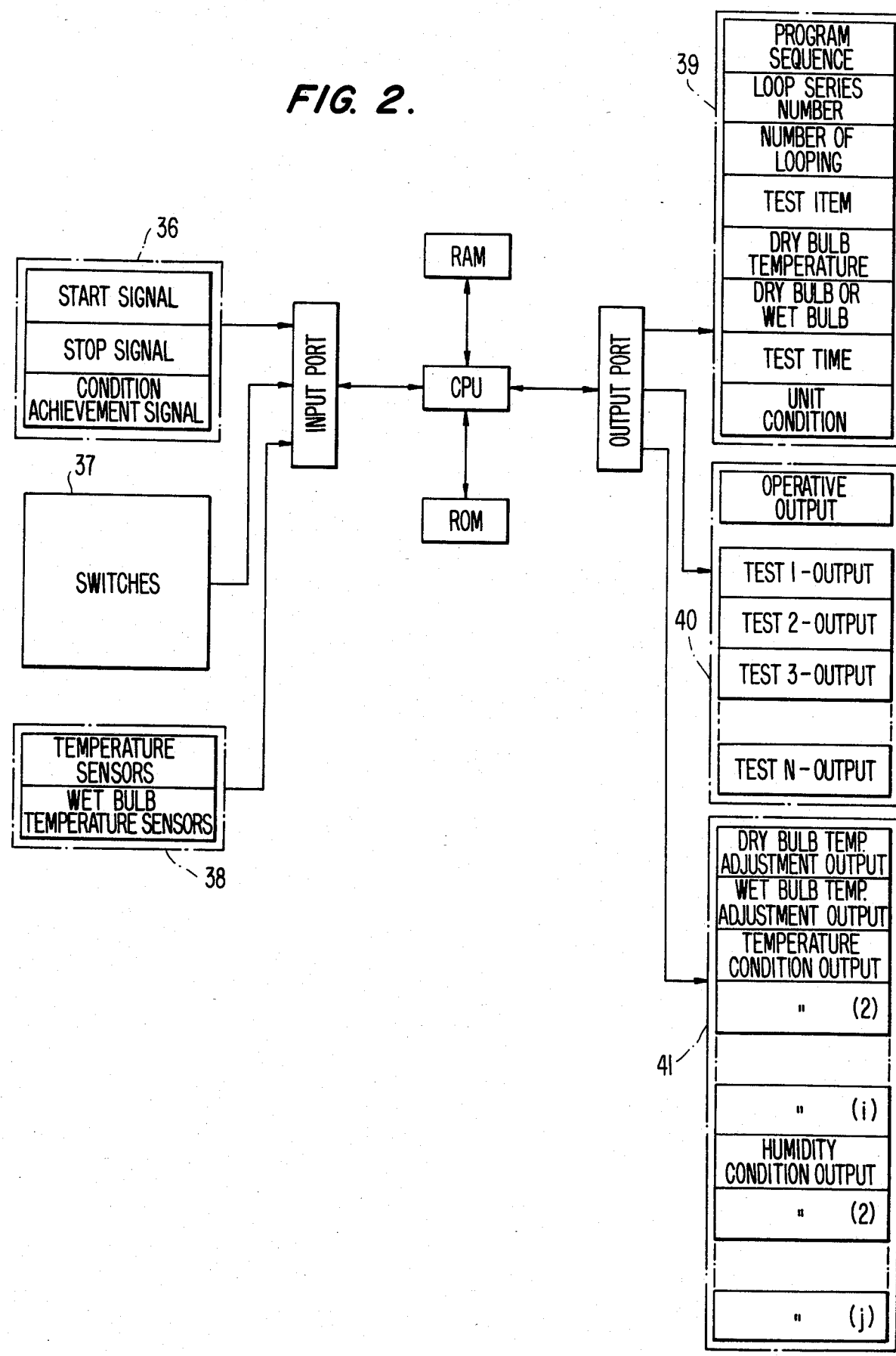
FIG. 2 is a block diagram of the apparatus of present invention.

FIG. 2 is a block diagram of the apparatus of the present invention. The central portion of the apparatus consists of a microcomputer. A signal 36 received from the control panel of the combination corrosion tester cosists of a start signal for starting the present apparatus operating, a stop signal for stopping the operation, and a condition-achieved signal indicating that a condition has been achieved. Signal lines for these signals are connected to appropriate terminals on the rear surface of the main frame. The group of switches denoted by 21 through 35 in FIG. 1 are denoted by 37 in this figure, and the group of display windows and indicator lamps denoted by 7 through 20 in FIG. 1 are denoted by 39. A number of temperature sensors 38 necessary for controlling the temperature and humidity within the testing tank of the combination corrosion tester are connected to the rear surface of the apparatus. Standard thermosensitive resistors, various thermocouples and thermistors are selected as appropriate as the temperature sensors, and they are used as pairs consisting of one each for dry bulb and wet bulb temperatures. When neither measurement nor control of humidity are needed, only dry bulb thermometers are connected.

Groups of relay output contacts 40 and 41 are arranged on the rear surface of the main frame as terminals or connectors. "Operative output" is generated after various settings of the apparatus are completed, and the mode is set to "display" mode. The circuitry of the apparatus is constructed so that the start switch of the control panel becomes operative only after this output has been generated. "Test 1-n outputs" are selectively generated in accordance with the set sequence of the test times, only during the test period, and operation may be carried out from the control panel under the testing conditions of the test item whose output is currently being generated.

Other outputs include a dry bulb temperature adjustment output for controlling the temperature, a wet bulb temperature adjustment output, temperature condition outputs (1) through (i), and humidity condition outputs (1) through (j). The temperature condition outputs and the humidity condition outputs are used for efficient adjustment of the temperature and humidity to desired settings. An example of the temperature condition outputs will now be described. When the temperature has been set below −20° C., temperature condition output (1) is turned on, and when the temperature condition has been set to within −20° C. to +20° C., temperature condition output (2) is turned on. When the condition has been set to within 20° C. to 40° C., temperature condition output (3) is turned on, and when the temperature has been set to within 40° C. to 90° C., temperature condition output (4) is turned on. When the temperature has been set to above 90° C., temperature condition output (5) is turned on. The temperature can be controlled to the set value under optimal conditions by changing the capacities of a refrigerator and a heater using these output contacts, so that the operation can be carried out efficiently and the adjustment accuracy can be improved. Exactly the same is true of the humidity condition outputs. These temperature and humidity condition outputs are selected as appropriate, and are used for forming the circuit of the control panel.

Figure 4:
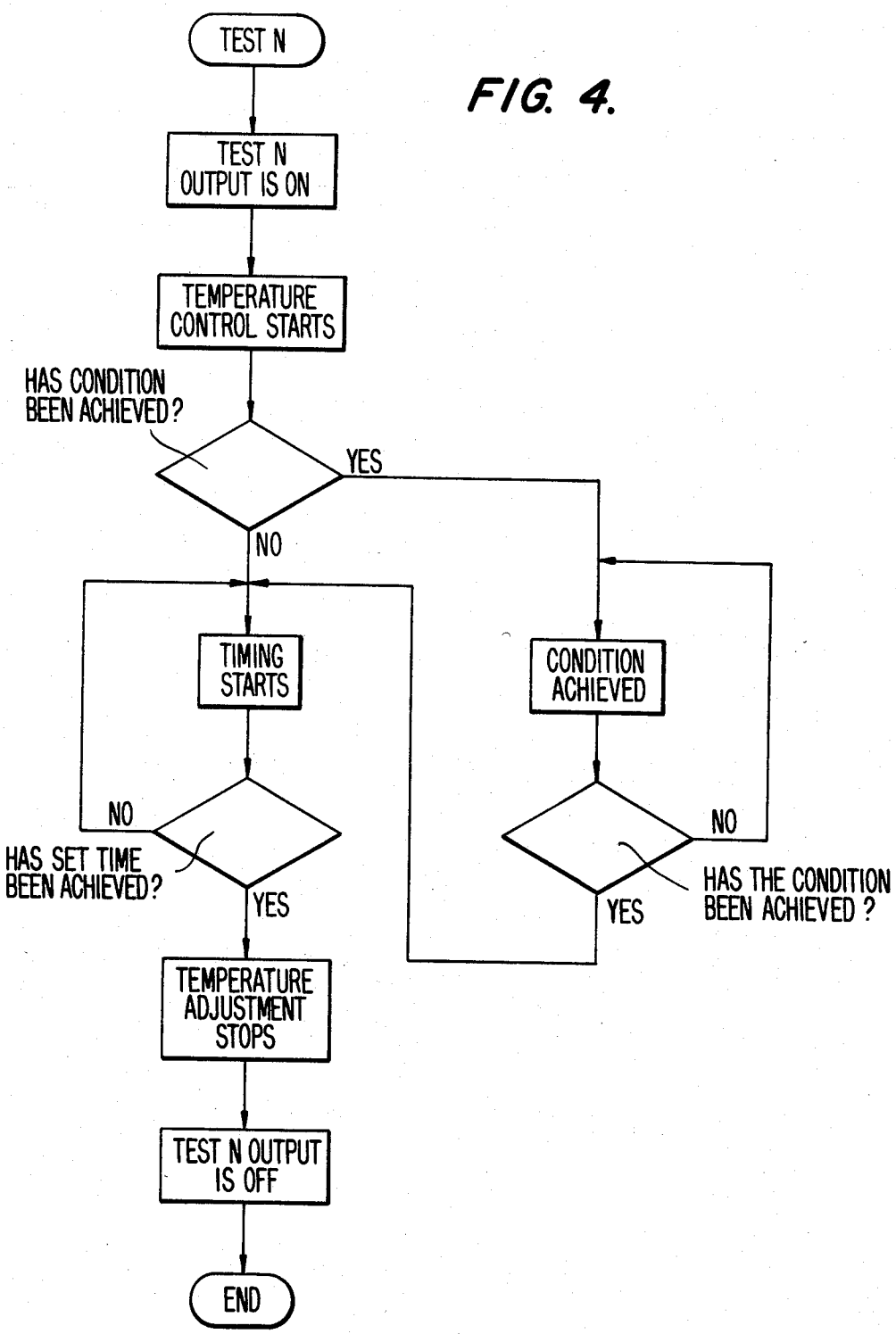
FIG. 4 is a flow chart illustrating the operation of the apparatus.

The flow of the program of the present invention is fundamentally the same as that of the prior invention Japanese Patent Application No. 083402/1983), but it differs in that functions for temperature and humidity adjustment are added. A flow chart of a subroutine for one test item is shown in FIG. 4.

PROGRAM EXAMPLE 1

Figure 5:
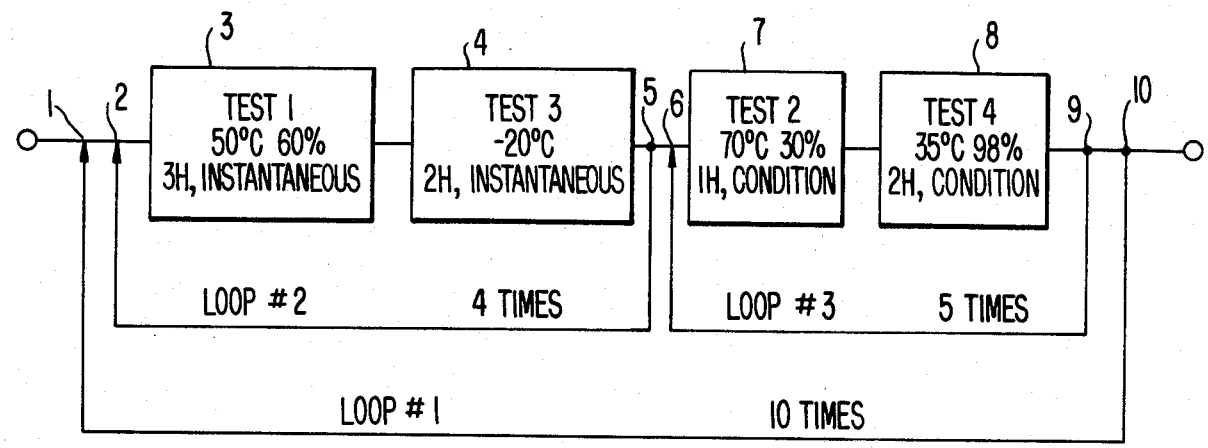
FIG. 5 shows an example of a combination of cycle tests.

Test details and the setting sequence when programming tests using the apparatus of the present invention will now be described, with reference to the cycle shown in FIG. 5, in order to clarify the functions of the apparatus. In FIG. 5, reference numerals ① through ⑩ correspond to the program sequence, and the program can be set in accordance with this sequence. The details of the test will be described in that order.

1: The outermost loop becomes Loop 1, it is repeated 10 times.
2: The next loop becomes Loop 2, it is repeated four times.
3: Test 1 is started within Loop 2. The conditions are as follows:
   Temperature: 50° C.,
   humidity: 60%,
   test time: 3 hours,
The measurement of time is made by an instantaneous operation.
4: Subsequently, Test 3 is conducted as an instantaneous operation at −20° C. for 2 hours.
5: The repeat range of the Loop 2 is completed. In other words, the next step is followed after the tests of steps (3) and (4) have been repeated four times.
6: The next loop becomes Loop 3, it is repeated five times.
7: Test 2 is started within Loop 3:
   temperature: 70° C.,
   humidity: 30%,
   time: 1 hour.
The measurement of time is done after the condition is achieved at which the temperature of the testing tank has reached 70° C.
8: Test 4 is then conducted:
   temperature: 35° C.,
   humidity: 98%,
   time: 2 hours after "condition achieved".
9: Repetition of Loop 3 is completed. Therefore, the tests of steps (7) and (8) are repeated five times, and the next step is followed.
10: Repetition Loop 1 is completed. Therefore, the cycle operation of this example is completed after the steps from (2) to (9) are repeated 10 times.

The sequence of storing these details as a program in the apparatus of the present invention is as follows:

The "set" switch 22 in FIG. 1 is pressed to put the apparatus in "set" mode. The program sequence display widow 7 indicates "001" and the program sequence is automatically incremented as the following operations are carried out.

Program sequence:
1: "loop start" "1" (set) "10" (set)
2: "loop start" "2" (set) "4" (set)
3: "test" "1" (set) "50° C." (set) "60%" (set) "3" (set) "instantaneous operation"
Remarks:
If the indicator lamp 17 is not lit when the humidity 60% is set, the temperature/humidity selector switch 31 must be pressed to turn on the humidity indicator lamp 31. "60" (set) is then input. Similarly, the indictor lamps 19 and 20 for the hour and minute units are selected by the hour/minute selector switch 32.
4: "test" "3" (set) "−20° C." (set) (set) [If there is no humidity, (set) is pressed twice] "2" (set) "instantaneous operation"
5: "loop end" "2" (set)
6: "loop start" "3" (set) "5" (set)
7: "test" "2" (set) "70° C." (set) "30%" (set) "1" (set) "after condition achieved"
8: "test" "4" (set) "35° C." (set) "98%" (set) "2" (set) "after condition achieved"
9: "loop end" "3" (set)
10: "loop end" "1" (set)

The items and numerals in inverted commas " " correspond to the switches 27 through 35 of FIG. 1, and (set) indicates that the input of a numeral has been completed. It is one of the switches in the group of numeric keys 30.

As is obvious from the description above, the apparatus of the present invention can be set sequentially in accordance with the program flow, after drawing up a system diagram of the cycle operation such as that shown in FIG. 5, and can be handled extremely easily.

PROGRAM EXAMPLE 2

In accordance with the present invention, program control is enabled in the same way as in the program setting sequence described already. Moreover, even if the program pattern differs for each test item, various test items can be executed under program control, and the usage range can be greatly expanded.

Figure 6:
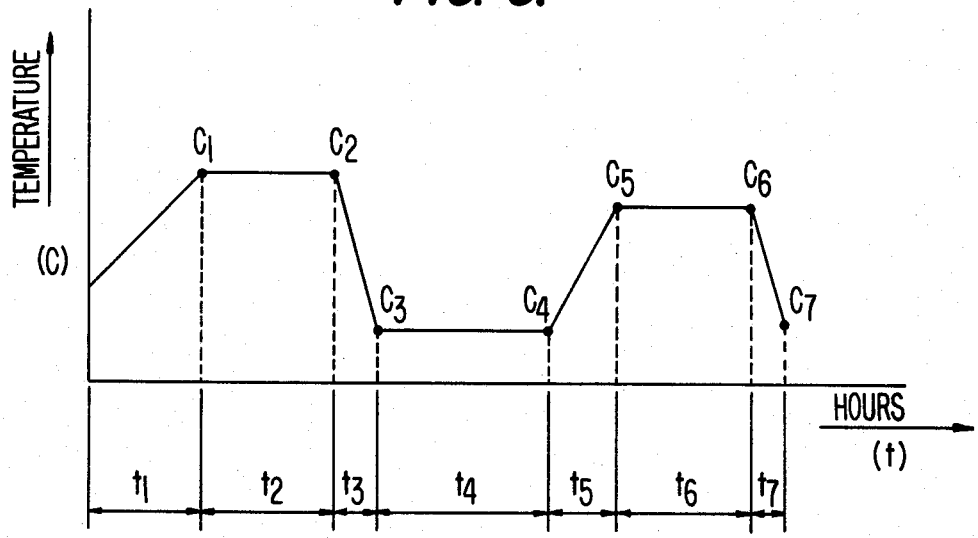
FIG. 6 shows an example of program control.

FIG. 6 shows an example of a program control pattern. Positions of temperature changes are indicated by broken lines, so the following description is given in accordance with the broken lines.
1: The temperature is raised from the current temperature to a temperature $C_1$ during a period of time $t_1$.
2: Temperature $C_1$ ($=C_2$) is held for a period of time $t_2$.
3: The temperature is reduced from temperature $C_2$ to a temperature $C_3$ during a period of time $t_3$.
4: Temperature $C_3$ ($=C_4$) is held during a period of time $t_4$.
5: The temperature is raised from temperature $C_4$ to $C_5$ during a period of time $t_5$.
6: Temperature $C_5$ ($=C_6$) is held for a period of time $t_6$.
7: The temperature is reduced from $C_6$ to $C_7$ during a period of time $t_7$.

In order to repeat these operations, steps 1 through 7 can be programmed in a loop with a specified number of repetitions, assuming that the temperature can be raised from $C_7$ to $C_1$ during the time $t_1$.

The sequence of setting the example of FIG. 6 in the apparatus of the present invention can be done in the following manner. The "program control" specification switch 35 of FIG. 1 is pressed to turn the program control indictor lamp 16 on. Setting is then done according to the sequence determined by the broken lines of FIG. 6. The test item is specified as n, but the same number can only be used throughout if only temperature tests are contemplated. If other test conditions are added, individual test item numbers must be input, and separate tests can be carried out for each section of broken lines.

```
1: "test" "n" (set) "C₁"
2: "test" "n" (set) "C₂" (set) "t₂" (set)
   .
   .
7: "test" "n" (set) "C₇" (set) "t₇" (set)
```

The sequence "test" "n" (set) can be deleted if the same number is used each time, and the next temperature value can be input by simply pressing the (set) key.

The example described above deals only with temperature, but of course humidity must be controlled concurrently with temperature. Therefore, humidity percentages or wet bulb temperatures must be set next to the temperature conditions, in the same way as in the example of FIG. 5. If the humidity conditions can be left as they are, without any control, they can be omitted by using only the (set) key.

As described above, the apparatus of the present invention enables the unrestricted preparation of various different cycle tests using only the programsetting operations. However, since the program contents are stored even after a halt in the operation and can be used again, operations such as "change38", "insert", "delete", and the like can be added.

The program is set in accordance with a program sequence with serial numbers if the number of a particular line is omitted, that portion can be regarded to be a delimiter of the program. Accordingly, if the contents of a few different cycle tests are set in advance, and if the header number of each cycle test is known, any desired cycle test can be selected by setting that header number during operation.

If a single test is input as a one-line program, only one test item can be performed as a single operation.

When providing operation control for a combination corrosion tester, the apparatus of the present invention can be freely set by the operator without any necessity of changing or modifying the circuitry. Accordingly a large number of test methods, that could never be accomplished by conventional systems, are now possible.

Moreover, since a "rest" mode, in which no conditions are added to a cycle test, can also be included in a cycle test, the testpiece can be subjected intermittently to a combination of tests in which the tests are not repeated continuously, but a "rest38 state is inserted between tests. In order to accomplish a "rest" test, it is necessary conventionally to stop the operation, but in accordance with the present invention this can be accomplished by simply inserting a suitable number of "rest" test items into the program.

The cost performance of the conventional system will now be compared with that of the apparatus of the present invention. Even if the number of test items increases, the apparatus needs only the addition of relays for the output circuits, so that the cost of the basic structure remains substantially constant. In accordance with the conventional system, on the other hand, the cost of the timers and temperature controllers increases in proportion to an increase in the number of the test items, and not only the number of components, but also the necessity of redesigning the circuit and increasing the number of wiring steps arises. If there are at least four test items, the present invention is more advantageous from the point of view of a simple cost comparison.

The functional advantages of the present invention over the prior art have already been described. The apparatus of the present invention will become indispensable for the control of combination corrosion testers.

What is claimed is:

1. A cycle sequence time/temperature controller for a combination corrosion tester, comprising:
    a means for setting a loop number and a number of repetitions thereof;
    a means for setting a sequence of test items within a loop, a test temperature, a test humidity and an operating time;
    a means for outputting a tester operation control signal;
    a means for enabling the start of an operation of said tester according to an external start signal;
    a means for providing an output corresponding to each test item for said set operating time only; and
    a means for providing an adjustment output signal for a dry bulb temperature and an adjustment output signal for a wet bulb temperature, each signal providing corresponding adjustments of said tester at said set test temperature and said set test humidity;
    wherein said controller has a display for displaying said loop number and said number of repetitions which are currently being effected, during its operation, and for further displaying: a test item number, the dry bulb temperature, one of either the wet bulb temperature or humidity, and the time elapsed, during its operation.

* * * * *